United States Patent [19]

Guentner et al.

[11] Patent Number: 5,420,259

[45] Date of Patent: May 30, 1995

[54] TRYPTANTHRINE DERIVATIVES

[75] Inventors: Andreas Guentner, Ilvesheim; Guenther Seybold, Neunofen; Gerhard Wagenblast, Weisenheim, all of Germany

[73] Assignee: BASF Aktiengesellschaft, Ludwigshafen, Germany

[21] Appl. No.: 310,996

[22] Filed: Sep. 23, 1994

Related U.S. Application Data

[63] Continuation of Ser. No. 879,916, May 8, 1992, abandoned.

[30] Foreign Application Priority Data

May 8, 1991 [DE] Germany ............. 41 14 990.4

[51] Int. Cl.$^6$ ................. C07D 487/04; C09B 56/12; C09B 57/00; D06P 1/44
[52] U.S. Cl. ................. 534/655; 544/245; 544/246; 106/493; 106/496
[58] Field of Search ............. 544/245, 246; 534/655

[56] References Cited

U.S. PATENT DOCUMENTS 4,666,526  5/1987  Rolf et al. ................. 106/309

FOREIGN PATENT DOCUMENTS 0151393  8/1985  European Pat. Off. .
287373  9/1915  Germany .

OTHER PUBLICATIONS

*The Chemistry of Synthetic Dyes* (K. Venkataroman, Editor), vol. IV, pp. 28–32 (1971).
*Kirk–Othmer Encyclopedia of Chemical Technology*, (3rd Ed.) (John Wiley & Sons, Publishers), vol. 17, pp. 871–889 (1982).

Dyes & Pigments, vol. 5, No. 5, 1984, pp. 189–207, M. Rolf, et al., "Neue, Hochechte Organische Pigmente".
J. Heterocyclic Chem., vol. 25, pp. 591 to 596, 1988 Conjugated Systems Derived From Piperazine-2,5-Dione Alan R. Katritzky, et al.
Chem. Ber., vol. 45, pp. 2244 to 2248, 1912 Uber Eine Neue Syntheses der Anthrachinonyl–Hydrazine A. Viertel et al.
Tetrahedron Lett., vol. 30, pp. 2625 and 2626, 1977 the Structure of Some Indolic Constituents in Couroupita Guaianensis Aubl. Jan Bergman, et al.
Tetrahedron, vol. 41, pp. 2883 and 2884, 1985 Structure Determination of Candidine, a Violet Indolic Constituent from Culture Solutions of Candida Lipolytica Jan Bergman, et al.
J. Chem. Soc. Perkin Trans. I, pp. 519 to 527, 1987 J. Chem. Soc. perkin Trans. Jan. 1987 Jan Bergman, et al.

*Primary Examiner*—Emily Bernhardt
*Attorney, Agent, or Firm*—Oblon, Spivak, McClelland, Maier & Neustadt

[57] ABSTRACT

Tryptanthrine derivative of the formula

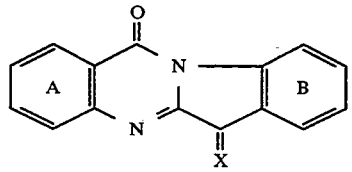

where the rings A and B may be benzofused and/or substituted and X is a radical which is derived from a CH-acidic heterocyclic structure which may have a further tryptanthrine radical or from a hydrazinoanthraquinone or, if one or both of the rings A and B are benzofused and/or substituted by phthaloyl, is furthermore oxygen, are used as colorants.

4 Claims, No Drawings

TRYPTANTHRINE DERIVATIVES

This application is a continuation of application Ser. No. 07/879,916, filed on May 8, 1992, now abandoned.

The present invention relates to novel tryptanthrine derivatives of the formula I

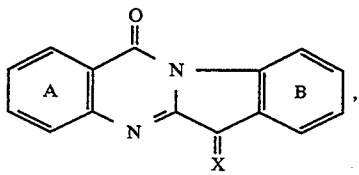

(I)

where the rings A and B are identical or different and independently of one another may each be benzofused and may each be monosubstituted to trisubstituted by halogen, $C_1$–$C_4$-alkyl, $C_1$–$C_4$-alkoxy, carboxyl, $C_1$–$C_4$-alkoxycarbonyl, carbamoyl or hydroxysulfonyl, or monosubstituted by phthaloyl, and X is a radical of the formula

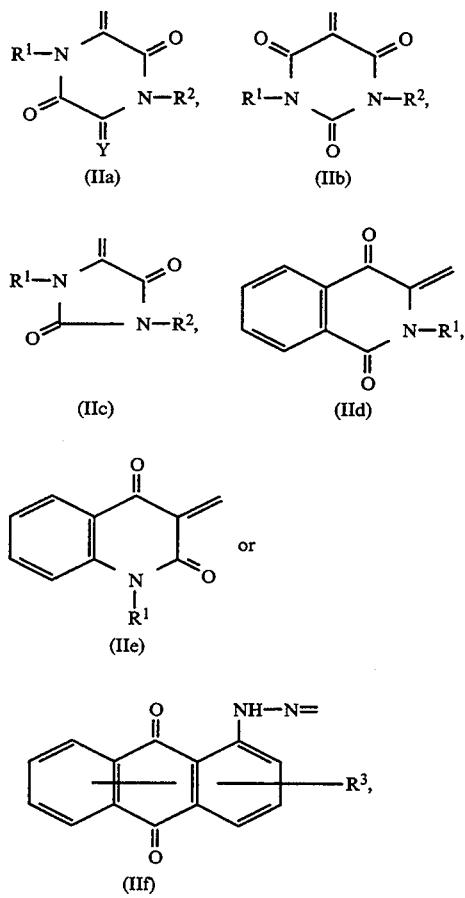

where $R^1$ and $R^2$ are identical or different and independently of one another are each hydrogen or $C_1$–$C_4$-alkyl, $R^3$ is hydrogen, $C_1$–$C_4$-alkyl, halogen or $C_1$–$C_4$-alkoxy, and Y is oxygen or a radical of the formula

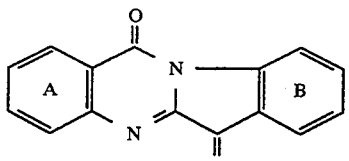

where the rings A and B each have the abovementioned meanings, or, if at least one of the rings A and B is benzofused and/or substituted by phthaloyl, X is furthermore oxygen, and the use of these compounds as colorants.

Tetrahedron Lett. 30 (1977), 2625–2626 describe tryptanthrine of the formula

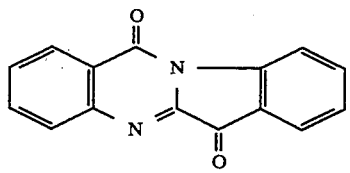

also referred to there as couropitine A, and some of its derivatives substituted by chlorine or bromine.

Furthermore, Tetrahedron 41 (1985), 2883–2884 discloses the condensates of typtanthrine with malodinitrile and 3-hydroxyindole.

J. Chem. Soc. Perkin Trans. I (1987), 519–527 describes a double tryptanthrine. Finally, German Patent 287,373 discloses the phenylhydrazone of tryptanthrine.

However, it has been found that these products have deficiencies when used as colorants.

It is an object of the present invention to provide novel tryptanthrine derivatives which have advantageous performance characteristics.

We have found that this object is achieved by the tryptanthrine derivatives of the formula I defined at the outset.

All alkyl groups occurring in the abovementioned formula I may be both straight-chain and branched.

Suitable substituents for the rings A and B, as well as for the radicals $R^1$, $R^2$ and $R^3$ are, for example, methyl, ethyl, propyl, isopropyl, butyl, isobutyl and sec-butyl.

Further suitable substituents for the rings A and B, as well as for the radicals $R^3$, are for example, methoxy, ethoxy, propoxy, isopropoxy, butoxy, fluorine, chlorine and bromine.

Further suitable substituents for the rings A and B are, for example, methoxycarbonyl, ethoxycarbonyl, propoxycarbonyl, isopropoxycarbonyl and butoxycarbonyl.

Tryptanthrine derivatives of the formula I where the rings A and B independently of one another may be benzofused and may be monosubstituted or disubstituted by chlorine or bromine or monosubstituted by phthaloyl are preferred.

Tryptanthrine derivatives of the formula I where X is one of the radicals of the formula IIa, IIc or IIf are also preferred.

Tryptanthrine derivatives of the formula I where X is a radical of the formula

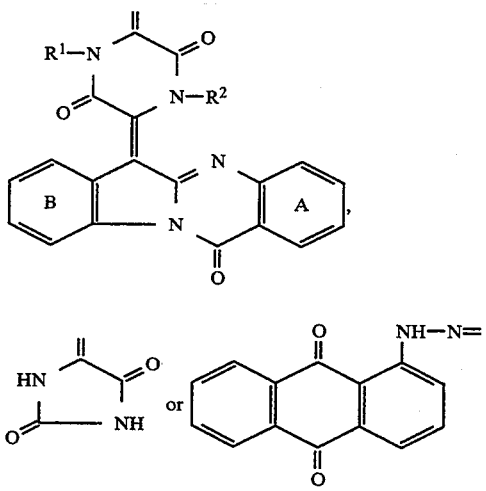

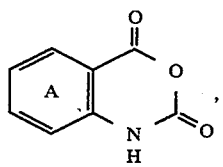  or  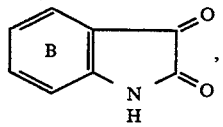

where R¹ and R² independently of one another are each hydrogen or methyl, in particular hydrogen, and the rings A and B each have the abovementioned meanings are particularly preferred.

The novel tryptanthrine derivatives of the formula I can be obtained by conventional methods.

For example, an isatoic anhydride of the formula

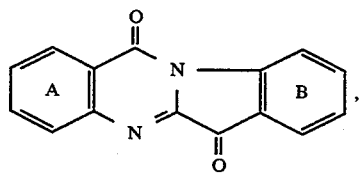 (II)

where the ring A has the abovementioned meanings, can be reacted with an isatin of the formula III

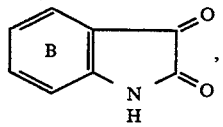 (III)

where the ring B has the abovementioned meanings, the reaction product formed being a tryptanthrine of the formula Ia

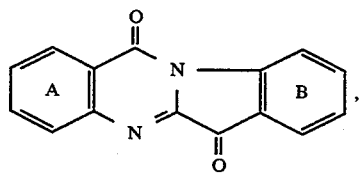 (Ia)

where the rings A and B each have the abovementioned meanings.

Isatoic anhydride II and isatin III are used, as a rule, in an equimolar ratio. The reaction can be carried out, for example, in pyridine as a diluent at from 95° to 110° C.

Those tryptanthrines of the formula I in which X has a meaning other than oxygen can be obtained by reacting a tryptanthrine Ia with a compound of the formula IV

ZH₂  (IV), where Z is a radical of the formula IIa, IIb, IIc, IId, IIe or IIf.

If Z is a radical of the formula IIa, IIb, IIc, IId or IIe, it is advantageous to use compounds in which R¹ and R² are each acetyl as starting materials.

The condensation reaction can generally be carried out successfully in N,N-dimethylformamide in the presence of a base, eg. triethylamine, or in acetic anhydride in the presence of an alkali metal acetate, eg. sodium acetate, at from 50° to 150° C. The molar ratio of tryptanthrine Ia to the compound IV is as a rule from 0.8:1 to 1.2:1.

In the preparation of the compounds of the formula I where X is the radical IIa in which Y is a radical of the formula

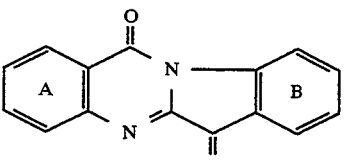

the molar ratio of tryptanthrine to piperazinedione is in general from 1:1 to 2.2:1. (The compound of the formula IVa

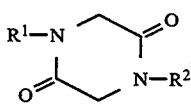 (IVa)

where R¹ and R² each have the abovementioned meanings, is defined as a piperazinedione.)

Similar reactions are disclosed in J. Heterocycl. Chem. 25 (1988), 591–596.

The compounds of the formula I where R¹ and R² are each C₁–C₄-alkyl can be obtained by alkylating the correspondingly unsubstituted =NH— compounds by a conventional method.

If Z in formula IV is the radical of the formula IIf, hydrazone formation is advantageously effected in N,N-dimethylformamide in the presence of glacial acetic acid at from 50° to 120° C. The 1-hydrazinoanthraquinones used as starting compounds are described in, for example, Chem. Ber. 45 (1912), 2244–2248.

The compounds of the formula I where the rings A and/or B are substituted with halogen can also be obtained by aromatic halogenation of the correspondingly unsubstituted tryptanthrine derivatives of the formula I by conventional methods.

The novel tryptanthrine derivatives can be advantageously used as colorants. They can be used alone or as a mixture with one another.

They can advantageously be employed as pigments for the production of surface coatings. They are also useful intermediates for the preparation of vat dyes.

The Examples which follow illustrate the invention.

EXAMPLE 1

14.7 g of isatin and 19.8 g of 4-chloroisatoic anhydride in 50 ml of pyridine were refluxed for 6 hours. Thereafter, the reaction mixture was cooled and the precipitate obtained was filtered off under suction, washed with methanol and dried. 6.3 g (23%) of the compound of the formula

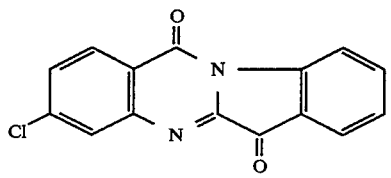

were obtained.

Analytical values (C$_{15}$H$_7$N$_2$O$_2$Cl): C 63.6 H 2.6 N 9.8 O 12.0 Cl 12.2 Melting point: 282° C.

The compounds shown in Table 1 below were obtained in a similar manner.

suction, washed with DMF and then with methanol and dried. 0.8 g of a dark powder of the formula

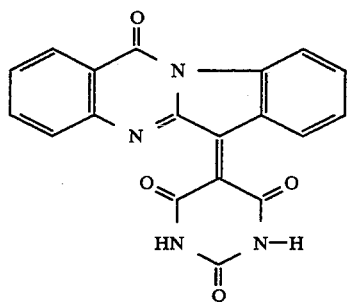

TABLE 1

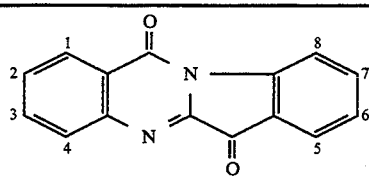

| Ex. No. | Substituents at ring positions | | | | | | Yield [%] | mp. [°C.] | Empirical formula Analytical values |
|---|---|---|---|---|---|---|---|---|---|
| | 1 | 2 | 3 | 4 | 5 | 6 | | | |
| 2 | Cl | | | Cl | | | 46 | 290–330 | C$_{15}$H$_{5.9}$N$_2$O$_2$Cl$_{2.1}$ × 0.3H$_2$O<br>C 55 H 21 N 8.7 O 11.4 Cl 22.9 |
| 3 | | Br | | Br | | | 31 | 269–286 | C$_{15}$H$_{5.7}$N$_2$O$_2$Br$_{2.3}$ × 2H$_2$O<br>C 41.5 H 1.4 N 6.4 O 8.0 Br 41.9 |
| 4 | | Br | | | | | 26 | 322 | C$_{15}$H$_7$N$_2$OBr<br>C 54.8 H 2.0 N 8.5 O 10.4 Br 23.6 |
| 5 | | Br | (Br) | Br | | | 32 | 355–364 | C$_{15}$H$_{5.7}$N$_2$O$_2$Br$_{2.3}$ × 0.2H$_2$O<br>C 41.2 H 1.7 N 6.4 O 7.9 Br 42.2 |
| 6 | | Br | (Br) | Br | Br | | 36 | 297–305 | C$_{15}$H$_{4.7}$N$_2$O$_2$Br$_{3.3}$ × 0.15H$_2$O<br>C 34.9 H 1.0 N 5.3 O 6.6 Br 54.1 |
| 7 | | Br | Cl | Cl | | | 37 | 304–314 | C$_{15}$H$_5$N$_2$O$_2$Cl$_{2.15}$Br$_{0.85}$ × 0.15H$_2$O<br>C 46.3 H 1.4 N 7.2 O 8.8 Cl 19.3 Br 17.3 |
| 8 | Cl | Cl | | Cl | | | 39 | 290–297 | C$_{15}$H$_5$N$_2$O$_2$Cl$_3$<br>C 51.1 H 1.5 N 8.0 O 9.5 Cl 29.8 |
| 9 | | Cl | | Br | | | 38 | 268–276 | C$_{15}$H$_{6.49}$N$_2$O$_2$Cl$_{1.13}$Br$_{0.38}$ × 0.1H$_2$O<br>C 56.2 H 2.1 N 8.7 O 10.4 Cl 12.5 Br 9.6 |
| 10 | | Cl | | Cl | | Br | 41 | 269–296 | C$_{15}$H$_{5.31}$N$_2$O$_2$BrCl$_{1.69}$ × 0.33H$_2$O<br>C 45.7 H 1.5 N 7.0 O 9.7 Cl 15.2 Br 20.4 |
| 11 | | 2,3 (fused benzene ring) | | | | | 30 | >300 | C$_{19}$H$_{10}$N$_2$O$_2$<br>C 75.9 H 3.5 N 9.4 O 11.0 |
| 12 | | | 3,4 (fused diketone) | | | | 40 | >300 | C$_{23}$H$_{10}$N$_2$O$_4$ × 0.2H$_2$O<br>C 71.9 H 2.8 N 7.1 O 17.5 |
| 13 | | | 3,4 (fused diketone) | | Br | | 34 | >360 | C$_{23}$H$_9$N$_2$O$_4$Br<br>C 60.7 H 2.2 N 6.2 O 15.2 Br 15.1 |

EXAMPLE 14

6.2 g of tryptanthrine in 30 ml of N,N-dimethylformamide (DMF) were heated at the boil for 5 hours in the presence of 1.7 g of triethylamine and 6.4 g of barbituric acid. After cooling, the product was filtered off under suction, washed with DMF and then with methanol and dried. 0.8 g of a dark powder of the formula remained.

Analytical values (C$_{19}$H$_{10}$N$_4$O$_4$): found C 63.2 H 4.3 N 13.4 O 18.5

EXAMPLE 15

35 g of 4-hydroxy-1-methylquinol-2-one in 300 ml of acetic anhydride and 50 g of sodium acetate were heated with 50 g of tryptanthrine for 2 hours at 110° C. The residue formed was filtered off under suction, washed with methanol and then with water and dried. 33.5 g of a reddish brown powder of the formula

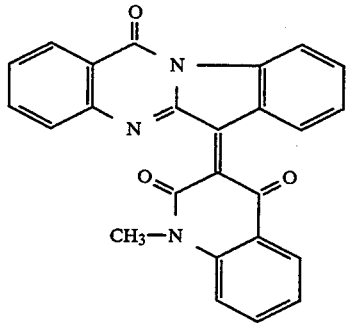

remained.

Analytical values $C_{25}H_{15}N_3O_3 \times H_2O$): found C 72.0 H 3.6 N 9.3 O 14.9

EXAMPLE 16

2.5 g of tryptanthrine in 50 ml of DMF and 0.6 ml of triethylamine were stirred with 1.8 g of acetylated hydantoin at 50° C. for 30 minutes. The residue was filtered off under suction, washed with DMF and with methanol and dried. 1.8 g of an orange powder of the formula

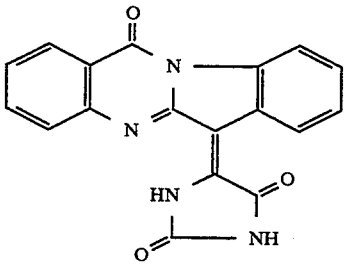

were obtained.

Analytical values ($C_{20}H_{12}N_4O_4$): C 46.2 H 3.3 N 15.1 O 17.1

The compounds shown in Table 2 below were obtained in a similar manner.

TABLE 2

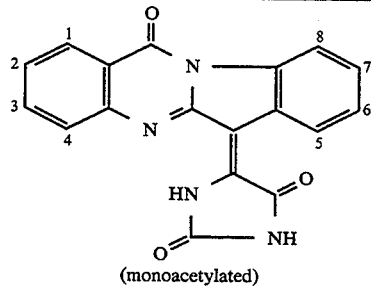

(monoacetylated)

| Ex. No. | Substituents in ring position 2 | 3 | 6 | Color | Empirical formula | Analytical values |
|---|---|---|---|---|---|---|
| 17 | | | Br | Orange | $C_{20}H_{11.12}N_4O_4Br_{0.88} \times 0.2H_2O$ | C 53.6 H 2.7 N 12.5 O 14.9 Br 15.8 |
| 18 | | 2,3 (fused benzo) | | Reddish brown | $C_{24}H_{14}N_4O_4$ | C 67.7 H 3.5 N 13.0 O 15.3 |
| 19 | | 3,4 (diacetyl) | | Brownish yellow | $C_{28}H_{14}N_4O_6$ | C 66.3 H 3.0 N 10.8 O 19.2 |
| 20 | | 3,4 (diacetyl) | Br | Brownish yellow | $C_{28}H_{13}N_3O_6Br$ | C 57.9 H 2.3 N 9.4 O 16.4 Br 12.9 (Cl 0.5) |

EXAMPLE 21

80 g of tryptanthrine were dissolved in 1000 ml of DMF and 100 ml of glacial acetic acid at from 105 to 110° C. 130.3 g of 1-hydrazinoanthraquinone were then introduced. The reaction mixture was stirred for 3 hours at 110° C. The mixture was then filtered under suction at 60° C. The residue was washed with DMF, with water and then with methanol and dried.

59 g of a red powder of the formula

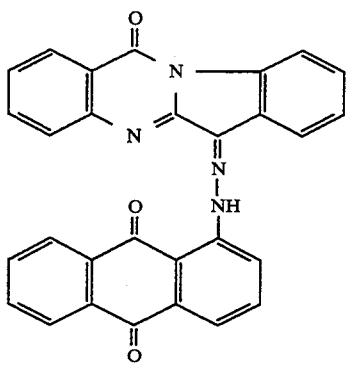

remained.

Analytical values ($C_{29}H_{16}N_4O_3$): C 74.3 H 3.5 N 11.7 O 10.5

The compounds shown in Table 3 below were obtained in a similar manner.

TABLE 3

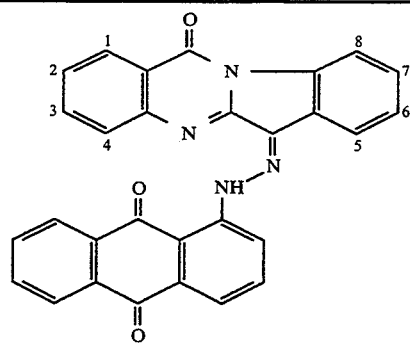

| Ex. No. | Substituents in ring position | | | | | | Color | Empirical formula Analytical values |
|---|---|---|---|---|---|---|---|---|
| | 1 | 2 | 3 | 4 | 5 | 6 | | |
| 22 | | Cl | | | | | Red | $C_{29}H_{15}N_4O_3Cl$ <br> C 68.9 H 3.1 N 11.3 O 10.3 Cl 6.5 |
| 23 | | | | | | Br | Red | $C_{29}H_{15}N_4O_3Br$ <br> C 63.2 H 2.8 N 10.1 O 9.1 Br 13.6 |
| 24 | | Cl | (Cl) | | | | Red | $C_{29}H_{14.3}N_4O_3Cl_{1.7} \times 0.15H_2O$ <br> C 66.1 H 2.8 N 10.5 O 9.6 Cl 11.2 |
| 25 | Cl | | | | | | Red | $C_{29}H_{15}N_4O_3Cl$ <br> C 69.1 H 3.1 N 11.3 O 10.0 CFl 6.9 |
| 26 | | Br | Br | | | | Red | $C_{29}H_{13.8}N_4O_3Br_{2.2} \times 0.4 H_2O$ <br> C 53.8 H 2.3 N 8.7 O 8.4 Br 26.9 |
| 27 | | Br | | | | | Red | $C_{29}H_{15}N_4O_3Br$ <br> C 63.4 H 2.7 N 10.1 O 9.0 Br 14.1 |
| 28 | | Br | (Br) | Br | | | Red | $C_{29}H_{14}N_4O_3Br_{2.4} \times 0.2H_2O$ <br> C 52.4 H 2.2 N 8.5 O 7.7 Br 28.6 |
| 29 | | Br | Br | Br | | Br | Brown | $C_{29}H_{12}N_4O_3Br_4$ <br> C 45.2 H 1.6 N 7.6 O 7.2 Br 39.0 |
| 30 | | Br | Cl | Cl | | | Brown | $C_{29}H_{13}N_4O_3BrCl_2$ <br> C 56.0 H 2.2 N 9.1 O 8.9 Br 11 Cl 12.4 |
| 31 | Cl | Cl | | Cl | | | Reddish brown | $C_{29}H_{13}N_4O_3Cl_3$ <br> C 60.1 H 2.4 N 9.8 O 9.1 Cl 18.3 |
| 32 | | Cl | | (Br) | | | Red | $C_{29}H_{14.49}N_4O_3Br_{0.39}Cl_{1.12} \times 0.3H_2O$ <br> C 63.9 H 2.8 N 10.1 O 9.6 Br 5.8 Cl 7.3 |
| 33 | | Cl | | Cl | | Br | Red | $C_{29}H_{13}N_4O_3BrCl_2$ <br> C 57.0 H 2.3 N 9.1 O 8.7 Br 12.1 Cl 10.1 |
| 34 | | 2,3-fused benzo | | | | | Dark brown | $C_{33}H_{18}N_4O_3 \times 0.2H_2O$ <br> C 75.4 H 3.5 N 10.6 O 9.6 |
| 35 | | 3,4-fused (CO)(CO)benzo | | | | | Dark brown | $C_{37}H_{18}N_4O_5$ <br> C 73.1 H 3.1 N 10.0 O 13.8 |

TABLE 3-continued

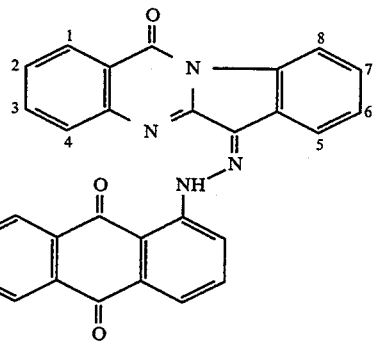

| Ex. No. | Substituents in ring position | | | | | | Color | Empirical formula Analytical values |
|---|---|---|---|---|---|---|---|---|
| | 1 | 2 | 3 | 4 | 5 | 6 | | |
| 36 | | | 3,4 — (diacetylbenzene) | | | Br | Dark brown | C37H17N4O5Br C 64.8 H 2.5 N 7.4 O 13.9 Br 10.8 |

EXAMPLE 37

7.44 g of tryptanthrine and 3 g of N,N-diacetylpiperazine-2,5-dione in 120 ml of DMF were refluxed in the presence of 1.5 g of triethylamine for 3 hours. The remaining residue was then filtered off under suction and washed with DMF and methanol. Drying gave 8.2 g of a dark powder of the formula

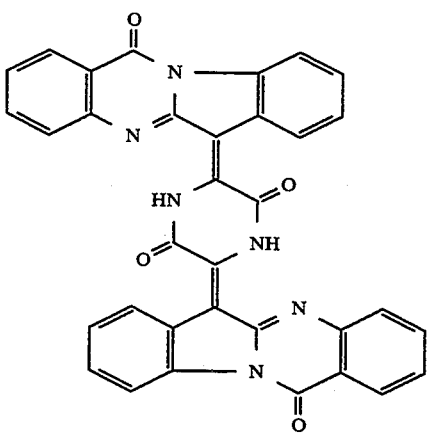

Analytical values ($C_{34}H_{18}N_6O_4$): C 70.4 H 3.3 N 14.5 O 11.8

The compounds shown in Table 4 below were obtained in a similar manner.

TABLE 4

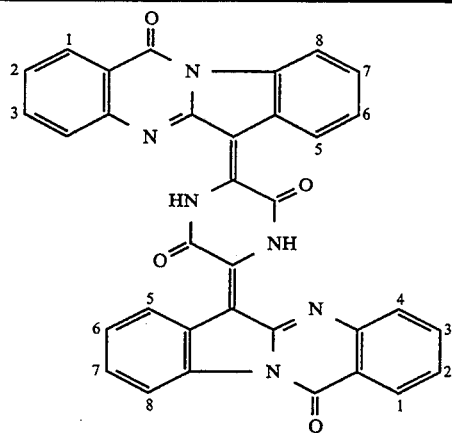

| Ex. No. | Substituents in ring position | | | | | Color | Empirical formula Analytical values |
|---|---|---|---|---|---|---|---|
| | 1 | 2 | 3 | 4 | 5 | 6 | | |
| 38 | | Cl | | | | | Dull violet | $C_{34}H_{16}N_6O_4Cl_2$<br>C 61.6 H 2.8 N 12.7 O 12.4 Cl 10.2 |
| 39 | | | | | | Br | Gray | $C_{34}H_{16}N_6O_4Br_2$<br>C 56.3 H 2.5 N 11.7 O 9.9 Br 19.4 |
| 40 | | Cl | | Cl | | | Dull violet | $C_{34}H_{14}N_6O_4Cl_4$<br>C 58.0 H 2.4 N 12.1 O 10.5 Cl 16.9 |
| 41 | | | Cl | | | | Dull brown | $C_{34}H_{16}N_6O_4Cl_2$<br>C 62.8 H 2.7 N 12.9 O 11.1 Cl 10.5 |
| 42 | Cl | | | | | | Dull violet | $C_{34}H_{14}N_{16}O_4Cl_2$<br>C 62.6 H 28 N 13.0 O 11.3 Cl 10.4 |
| 43 | Cl | | | | | | Gray | $C_{34}H_{14}N_6O_4Cl_4$<br>C 57.3 H 2.6 N 11.8 O 10.4 Cl 18.2 |
| 44 | | Cl | Cl | Cl | | | Dull blue | $C_{34}H_{12}N_6O_4Cl_6$<br>C 51.3 H 1.7 N 10.5 O 9.4 Cl 26.9 |
| 45 | | Br | | Br | | | Dull violet | $C_{34}H_{14}N_6O_4Br_4$<br>C 43.8 H 1.7 N 9.0 O 8.0 Br 37.3 |
| 46 | | | (SO₃)Na | | | | Dull blue | $C_{34}H_{16.3}N_6O_{14.2}S_{1.7}Na_{1.7} \times H_2O$<br>C 46.8 H 4.2 N 9.8 O 27.7 S 6.1 Na 5.1 |
| 47 | | Br | | | | | Dull blue | $C_{34}H_{16}N_6O_4Br_2$<br>C 55.4 H 2.6 N 11.5 O 10.1 Br 20.2 |
| 48 | | Br | (Br) | Br | | (Br) | Gray | $C_{34}H_{11.5}N_6O_4Br_{6.5} \times 0.75H_2O$<br>C 37.1 H 1.2 N 7.6 O 6.9 Br 47.2 |
| 49 | | Br | Br | Br | | | Grayish violet | $C_{34}H_{12}N_6O_4Br_2Q_4$<br>C 47.7 H 1.7 N 9.7 O 8.7 Br 15.4 Cl 17.1 |
| 50 | Cl | Cl | | Cl | | | Grayish violet | $C_{34}H_{12}N_6O_4Cl_6$<br>C 52.1 H 1.8 N 10.5 O 9.2 Cl 26.0 |
| 51 | | Cl | | (Br) | | | Gray | $C_{34}H_{14.9}N_6O_4Br_{0.9}Cl_{2.2} \times 0.4H_2O$<br>C 56 H 2.3 N 11.3 O 9.6 Br 9.7 Cl 10.8 |
| 52 | | Cl | | (Cl) | | Br | Brownish gray | $C_{34}H_{13.2}N_6O_4Br_{1.85}Cl_{2.95} \times 1.3H_2O$<br>C 48 H 2.3 N 10 O 9.9 Br 17.3 Cl 12.2 |
| 53 | | 2,3-fused benzo | | | | | Violet | $C_{42}H_{22}N_6O_4 \times 0.7H_2O$<br>C 73.3 H 3.4 N 12.2 O 10.9 |
| 54 | | | 3,4-diacetyl | | | | Violet | $C_{50}H_{22}N_6O_8 \times H_2O$<br>C 70.3 H 2.9 N 9.9 O 16.4 |
| 55 | | | 3,4-diacetyl | | | | Black | $C_{50}H_{20}N_6O_8Br_2$<br>C 60.5 H 2.0 N 8.1 O 4.6 Br 13.9 |

EXAMPLE 56

11.5 g of the compound from Example 37 in 70 ml of DMF and 2.9 g of sodium hydride were initially taken. 6 g of methyl iodide were added dropwise to the resulting blue solution at room temperature. The mixture was stirred for 3 hours at room temperature and filtered under suction, and the residue was washed with DMF, methanol and hot water and dried. 7.7 g of a dark powder of the formula

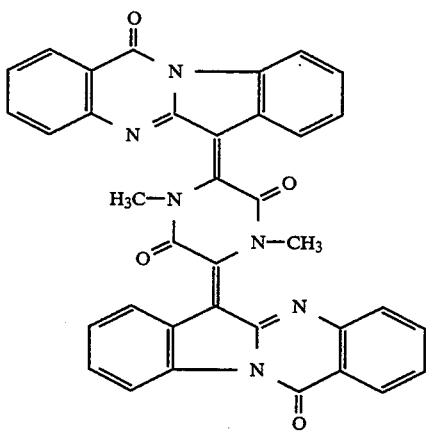

mp.: >350° C.

remained. Analytical values $(C_{36}H_{22}N_6O_4 \times 0.6\ H_2O)$: C 70.3 H 3.6 N 14.0 O 12.0

We claim:

1. A compound of the formula I

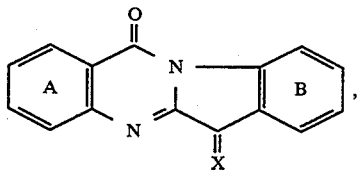

(I)

where the rings A and B are identical or different and independently of one another may each be benzofused and where the rings A and B may each be monosubstituted to trisubstituted by halogen, $C_1$–$C_4$-alkyl, $C_1$–$C_4$-alkoxy, carboxyl, $C_1$–$C_4$-alkoxycarbonyl, carbamoyl or hydroxysulfonyl, or monosubstituted by phthaloyl, and X is a radical of the formula

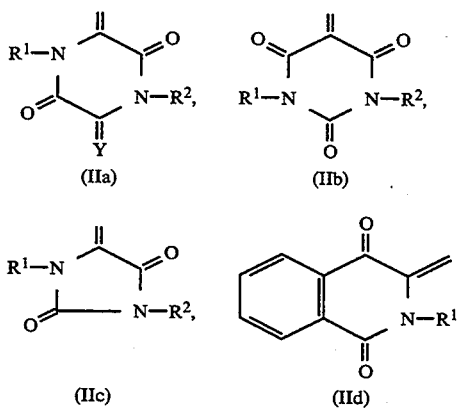

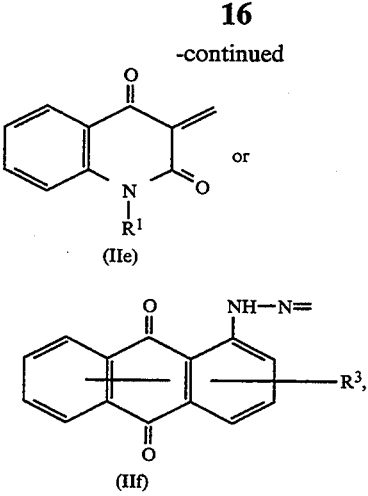

where $R^1$ and $R^2$ are identical or different and independently of one another are each hydrogen or $C_1$–$C_4$-alkyl, $R^3$ is hydrogen, $C_1$–$C_4$-alkyl, halogen or $C_1$–$C_4$-alkoxy, and Y is oxygen or a radical of the formula

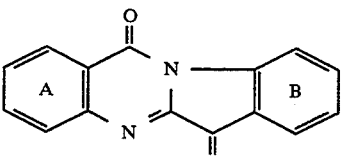

wherein the rings A and B each have the abovementioned meanings, or, if at least one of the rings A and B in formula I is benzofused or substituted by phthaloyl, X is furthermore oxygen.

2. A tryptanthrine derivative as claimed in claim 1, wherein the rings A and B independently of one another may be benzofused and may be monosubstituted or di-substituted by chlorine or bromine or monosubstituted by phthaloyl.

3. A tryptanthrine derivative as claimed in claim 1, wherein X is a radical of the formula IIa, IIc or IIf.

4. A tryptanthrine derivative as claimed in claim 1, wherein X is a radical of the formula

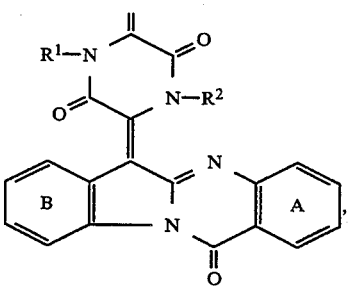

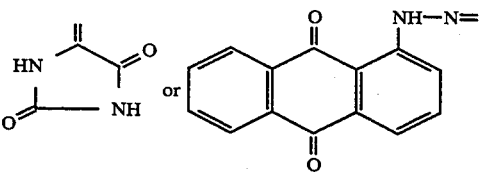

where $R^1$ and $R^2$ independently of one another are each hydrogen and methyl, and the rings A and B each have the meanings stated in claim 1.

* * * * *

UNITED STATES PATENT AND TRADEMARK OFFICE
CERTIFICATE OF CORRECTION

PATENT NO. : 5,420,259
DATED : May 30, 1995
INVENTOR(S) : Andreas GUENTNER, et al.

It is certified that error appears in the above-indentified patent and that said Letters Patent is hereby corrected as shown below:

On the title page, Item [75], the second inventor's city of residence should read:

--Neuhofen--

Signed and Sealed this

Twenty-fifth Day of July, 1995

Attest:

BRUCE LEHMAN

*Attesting Officer*     *Commissioner of Patents and Trademarks*